United States Patent
Bergman et al.

(10) Patent No.: US 8,512,649 B2
(45) Date of Patent: Aug. 20, 2013

(54) DUAL INLET MICROCHANNEL DEVICE AND METHOD FOR USING SAME

(71) Applicants: Richard Bergman, Horseheads, NY (US); Mark Alan Lewis, Horseheads, NY (US); Cheng-Chung Li, Painted Post, NY (US); William James Miller, Horseheads, NY (US)

(72) Inventors: Richard Bergman, Horseheads, NY (US); Mark Alan Lewis, Horseheads, NY (US); Cheng-Chung Li, Painted Post, NY (US); William James Miller, Horseheads, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 13/679,300

(22) Filed: Nov. 16, 2012

(65) Prior Publication Data

US 2013/0071935 A1    Mar. 21, 2013

Related U.S. Application Data

(60) Division of application No. 13/038,005, filed on Mar. 1, 2011, now Pat. No. 8,257,665, which is a division of application No. 11/983,327, filed on Nov. 8, 2007, which is a continuation-in-part of application No. 11/784,130, filed on Apr. 5, 2007, now Pat. No. 7,824,624.

(60) Provisional application No. 60/790,188, filed on Apr. 7, 2006.

(51) Int. Cl.
*B01L 3/00* (2006.01)

(52) U.S. Cl.
USPC .......................................... 422/503

(58) Field of Classification Search
USPC ........................................... 422/503
See application file for complete search history.

(56) References Cited

U.S. PATENT DOCUMENTS

| | | | |
|---|---|---|---|
| 4,815,843 A | 3/1989 | Tiefenthaler et al. | 356/128 |
| 5,798,215 A | 8/1998 | Cathey et al. | 435/7.9 |
| 6,200,814 B1 | 3/2001 | Malmqvist et al. | 436/52 |
| 6,418,968 B1 | 7/2002 | Pezzuto et al. | 137/833 |
| 6,526,812 B2 | 3/2003 | Martin et al. | 73/61.55 |
| 6,698,454 B2 | 3/2004 | Sjölander et al. | 137/885 |
| 6,994,826 B1 | 2/2006 | Hasselbrink et al. | 422/100 |
| 7,175,980 B2 | 2/2007 | Qiu et al. | 435/4 |
| 8,372,355 B2 * | 2/2013 | Zhou et al. | 422/502 |

(Continued)

FOREIGN PATENT DOCUMENTS

| | | |
|---|---|---|
| EP | 0 153 110 | 8/1985 |
| EP | 1 927 401 | 6/2008 |
| WO | 01/25137 | 4/2001 |
| WO | WO03/002985 | 1/2003 |
| WO | WO2005/043154 | 5/2005 |
| WO | WO2006/102516 | 9/2006 |

OTHER PUBLICATIONS

U.S. Appl. No. 60/817,724, filed Jun. 30, 2006, W.J. Miller et al.
Email correspondence for telephone interview on May 7, 2012. Three pages.

*Primary Examiner* — Lore Jarrett
(74) *Attorney, Agent, or Firm* — Thomas R. Beall; William J. Tucker, Esq.

(57) ABSTRACT

A dual inlet microchannel device and a method for using the device to perform a flow-through kinetic assay are described. A microplate having an array of the dual inlet microchannel devices and in particular their specially configured flow chambers is also described. Several embodiments of the dual inlet microchannel devices and specially configured flow chambers are also described.

10 Claims, 15 Drawing Sheets

(56) References Cited

U.S. PATENT DOCUMENTS

| | | | |
|---|---|---|---|
| 2003/0022388 A1 | 1/2003 | Roos et al. | 436/164 |
| 2003/0049862 A1 | 3/2003 | He et al. | 436/180 |
| 2004/0084311 A1 | 5/2004 | Okamoto et al. | 204/450 |
| 2005/0199076 A1 | 9/2005 | Tidare et al. | 73/863.01 |
| 2006/0106557 A1 | 5/2006 | Fontaine et al. | 702/87 |
| 2007/0020689 A1 | 1/2007 | Caracci et al. | 435/7.1 |
| 2008/0247907 A1* | 10/2008 | Bergman et al. | 422/68.1 |

* cited by examiner

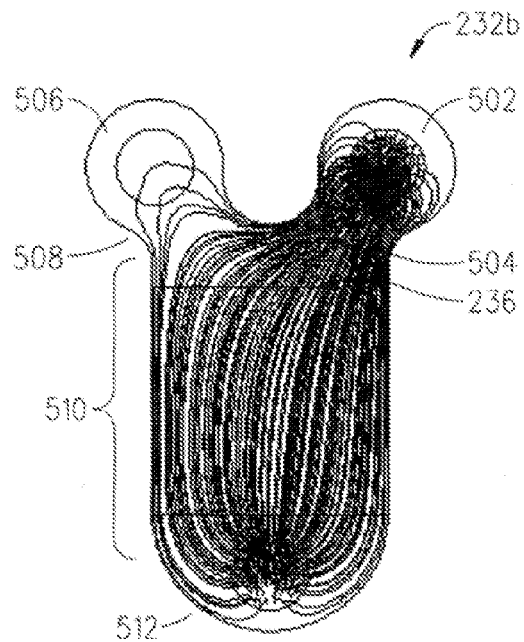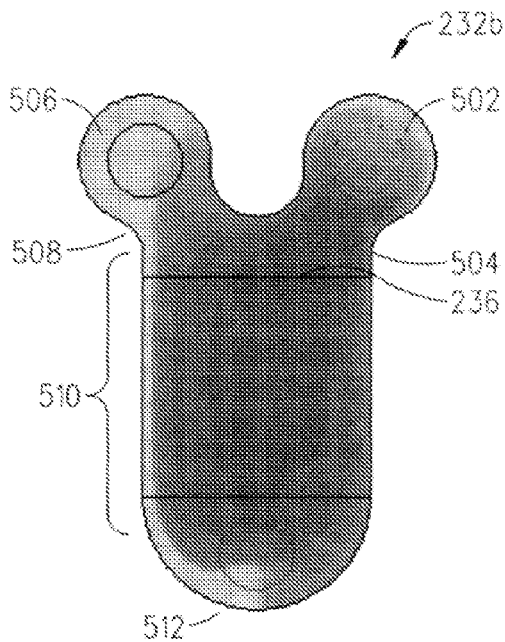
FIG. 6A    FIG. 6B
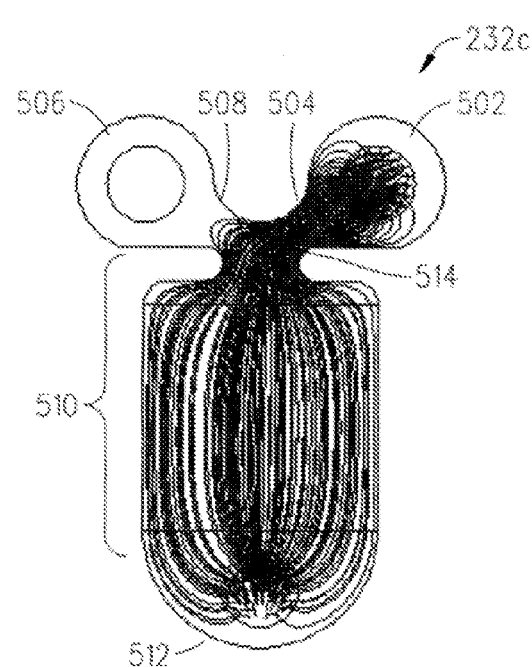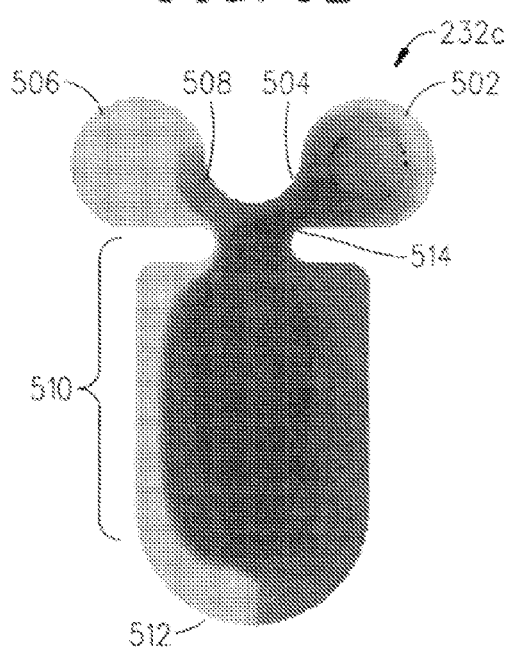
FIG. 6C    FIG. 6D

DUAL INLET MICROCHANNEL DEVICE AND METHOD FOR USING SAME

CLAIM OF PRIORITY

This application is a divisional application of U.S. patent application Ser. No. 13/038,005 filed on Mar. 1, 2011, now U.S. Pat. No. 8,257,665, which is a divisional application of U.S. patent application Ser. No. 11/983,327 filed on Nov. 8, 2007, now pending, which is a continuation-in-part application of U.S. patent application Ser. No. 11/784,130 filed on Apr. 5, 2007, now U.S. Pat. No. 7,824,624

The entire disclosure of publications, patents, and patent documents mentioned herein are incorporated by reference.

BACKGROUND

The disclosure relates to a dual inlet microchannel device and a method for using the dual inlet microchannel device to perform a flow-through kinetic assay.

SUMMARY

In embodiments, the disclosure provides a dual inlet microchannel device comprising a body having formed therein: a first fluid inlet; a second fluid inlet; a fluid outlet; and a flow chamber.

In embodiments, the disclosure provides a microplate incorporating the dual inlet microchannel device as describe herein.

In embodiments, the disclosure provides a method for performing a flow-through kinetic assay using the dual inlet microchannel device.

DETAILED DESCRIPTION

Figure 1A:
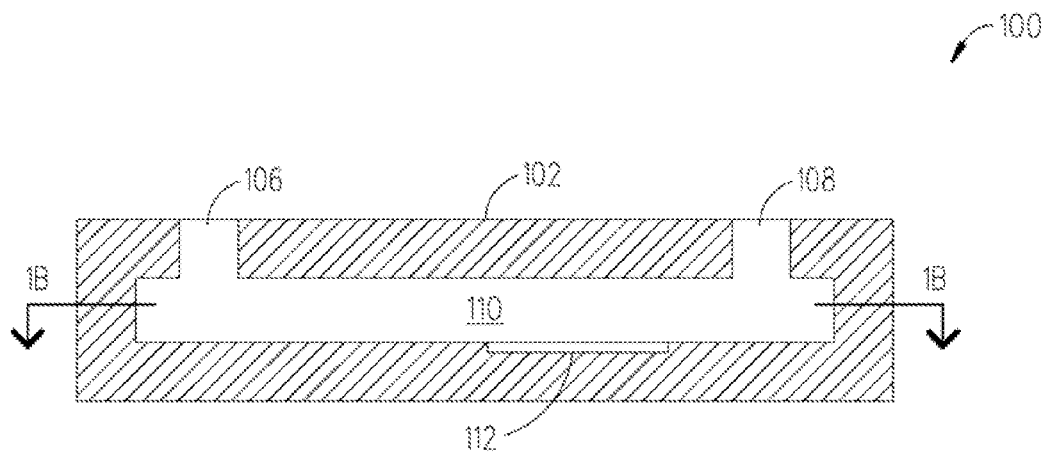
FIGS. 1A-1B are diagrams of a dual inlet microchannel device, in embodiments of the disclosure.

Various embodiments of the disclosure are described in detail with reference to drawings, if any. Reference to various embodiments does not limit the scope of the invention, which is limited only by the scope of the claims attached hereto. Additionally, any examples set forth in this specification are not limiting and merely set forth some of the many possible embodiments for the claimed invention.

The indefinite article "a" or "an" and its corresponding definite article "the" as used herein means at least one, or one or more, unless specified otherwise.

"Include," "includes," or like terms means including but not limited to.

"About" modifying, for example, the quantity of an ingredient in a composition, concentrations, volumes, process temperature, process time, yields, flow rates, pressures, and like values, and ranges thereof, employed in describing the embodiments of the disclosure, refers to variation in the numerical quantity that can occur, for example, through typical measuring and manipulation procedures; through inadvertent error in these procedures; through differences in the manufacture, source, or purity of starting materials or ingredients used to carry out the methods; and like considerations. The term "about" also encompasses amounts that differ due to, for example, aging of a formulation having a particular initial concentration, or mixture, and amounts that differ due to processing a formulation with a particular initial concentration, or mixture. Whether modified by the term "about" the claims appended hereto include equivalents to these quantities.

"Optional" or "optionally" or like terms generally refer to, for example, that the subsequently described event or circumstance can or cannot occur, and that the description includes instances where the event or circumstance occurs and instances where it does not.

"Consisting essentially of" in embodiments refers, for example, a dual inlet microchannel device comprising a body having formed therein: a first fluid inlet; a second fluid inlet; a fluid outlet; and a flow chamber, as defined herein, a microplate incorporating the dual inlet microchannel device as describe herein, a method for performing a flow-through kinetic assay using the dual inlet microchannel device as describe herein, and can include the components or steps listed in the claim, plus other components or steps that do not materially affect the basic and novel properties of the article, device, apparatus, system, and methods of making and use of the disclosure, such as a particular reactant, a particular additive or ingredient, a particular agent, a particular surface condition, or like structure, material, process, or computational variable selected.

Many areas of biological research use microchannel devices with embedded sensors to help perform increasingly sensitive and time-constrained flow-through kinetic assays. These flow-through kinetic assays are performed to detect biomolecular interactions such as material bindings, adsorptions, and like interactions that are helpful, for example, with testing new drugs. A typical flow-through kinetic assay is performed by first immobilizing a target on a sensing surface within a microchannel, and then flowing a buffer solution over the sensing surface to establish a baseline measurement. Then, a drug solution (or analyte solution) is flowed through the microchannel for a prescribed period of time, often called the association time, to enable the detection of an association response. Next, the buffer solution is flowed again through the microchannel to enable the detection of an dissociation response. The sensor responses during these steps are used to calculate the rate at which the drug associates with the immobilized target and then dissociates from the immobilized target. The response times, particularly during the association phase, can be on the order of about 1-100 seconds. Thus, to be able to monitor the shortest response times it is helpful that the switching time between the flowing of the buffer solution, the drug solution and then the buffer solution again be at least as short, and preferably much shorter than the time it takes the drug to completely bind to the immobilized target. Otherwise, the resulting kinetic response will be confounded by the slow fluidic switching. Accordingly, a challenge in the design of a microchannel device (or microfluidic flow cell) and the fluidic system (which supplies the buffer solution and the drug solution) is to minimize this switch time so faster sensor responses can be resolved. This and other challenges are satisfied by a dual inlet microchannel device and method of the disclosure.

In embodiments, an array of the dual inlet microchannel devices, and in particular their specially configured flow chambers, can be incorporated within a microplate. Several embodiments of the dual inlet microchannel devices and specially configured flow chambers are also described.

In embodiments, the flow chamber can include, for example: i) a first flow restrictive mechanism (i.e., a restrictor; e.g., porous material, weir, flow restrictive neck) associated with the first fluid inlet; ii) a second flow restrictor (e.g., porous material, weir, flow restrictive neck) associated with the second fluid inlet; iii) a central portion having one corner of one end associated with the first flow restrictor and another corner of the one end associated with the second flow restrictor; and iv) an outlet portion associated with the fluid outlet and an opposite end of the central portion, wherein the opposite end is directly opposite from both an opening of the one corner and an opening of the another corner associated with the one end of the central portion. The disclosure also includes a method for performing a flow-through kinetic assay using the dual inlet microchannel device.

In embodiments, the disclosure provides a microplate comprising: an upper plate including a top surface, a body, and a bottom surface, where the top surface has located thereon a sealing substance which has one or more fluid delivery-removal sealing interfaces where each fluid delivery-removal sealing interface can have at least two fluid inlet ports and at least one fluid outlet port; the body having one or more fluid delivery-removal channels extending therethrough where each fluid delivery-removal channel has at least two fluid inlet channels and at least one fluid outlet channel which are respectively aligned with the at least two fluid inlet ports and the at least one fluid outlet port that are located within the corresponding fluid delivery-removal sealing interface of the sealing substance; and a lower plate including a top surface which is attached to the bottom surface of the upper plate such that one or more flow chambers are present therebetween, where each one of the flow chambers is in fluid communication with a corresponding one of the fluid delivery-removal channels extending through the body of the upper plate. In embodiments, each flow chamber can further include, for example: i) a first flow restrictor (e.g., porous material, weir, flow restrictive neck) associated with one of the corresponding fluid inlet ports; ii) a second flow restrictor (e.g., porous material, weir, flow restrictive neck) associated with another one of the corresponding fluid inlet ports; iii) a central portion having one end associated with the first flow restrictor and the second flow restrictor; and iv) an outlet portion associated with the corresponding fluid outlet port and an opposite end of the central portion. The disclosure also includes a method for performing a flow-through kinetic assay using the microplate.

Figure 1B:
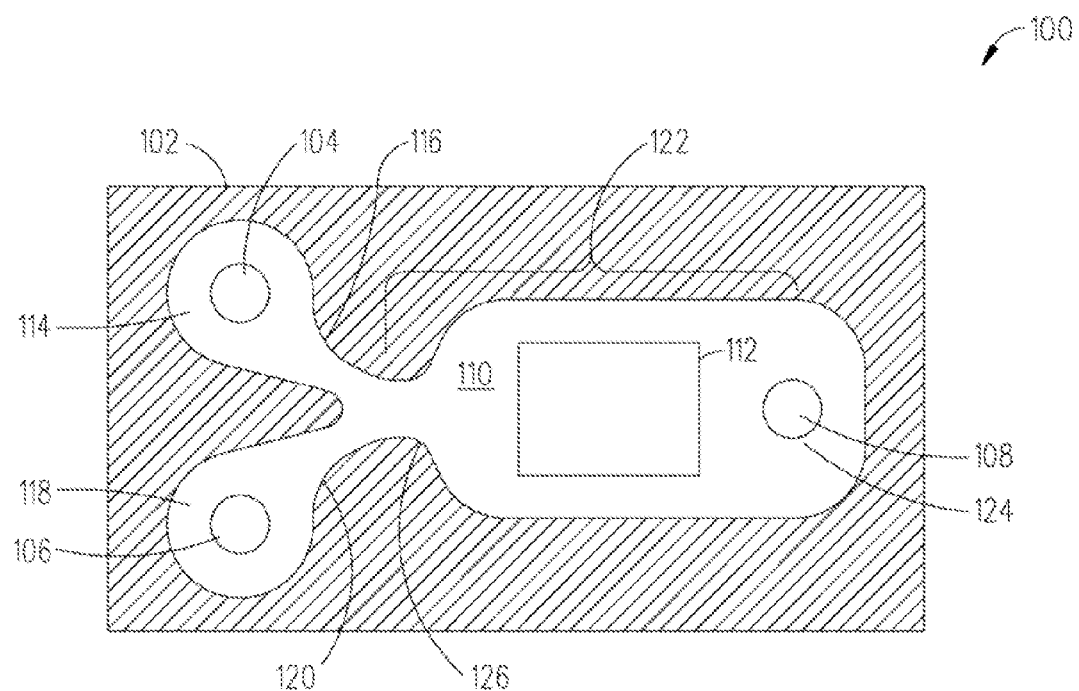

Referring to FIGS. 1A-1B, there are respectively illustrated a cross-sectional side view and a cross-sectional top view of a dual inlet microchannel device 100 in accordance with the disclosure. The dual inlet microchannel device 100 includes a body 102 having located therein a first fluid inlet 104, a second fluid inlet 106, a fluid outlet 108, a flow chamber 110, and an optional sensor 112. The flow chamber 110 includes a first inlet portion 114, a first flow restrictive neck 116 (flow restrictor 116), a second inlet portion 118, a second flow restrictive neck 120 (flow restrictor 120), a central portion 122, and an outlet portion 124. As can be seen, the first fluid inlet 104 is in fluid communication with the first inlet portion 114. The first inlet portion 114 is in fluid communication with the first flow restrictive neck 116. Likewise, the second fluid inlet 106 is in fluid communication with the second inlet portion 118. The second inlet portion 106 is in fluid communication with the second flow restrictive neck 120. The first and second flow restrictive necks 116 and 120 are in fluid communication with one end of the central portion 122. If desired, the central portion 122 can have a flow restrictive neck 126 which is in fluid communication with the first and second flow restrictive necks 116 and 120. The sensor 112 if used would have a sensing surface that would be located within the central portion 122. Lastly, the outlet portion 124 would be in fluid communication with the fluid outlet 108 and an opposite end of the central portion 122. The dual inlet microchannel device 100 and in particular the flow chamber 110 is specially configured so as to minimize the fluid switching time that is desired when performing a flow-through kinetic assay. A discussion of the specially configured flow chamber 110 is provided below with respect to an exemplary microplate 200 which has an array of the specially configured flow chambers incorporated therein.

Figure 2A:
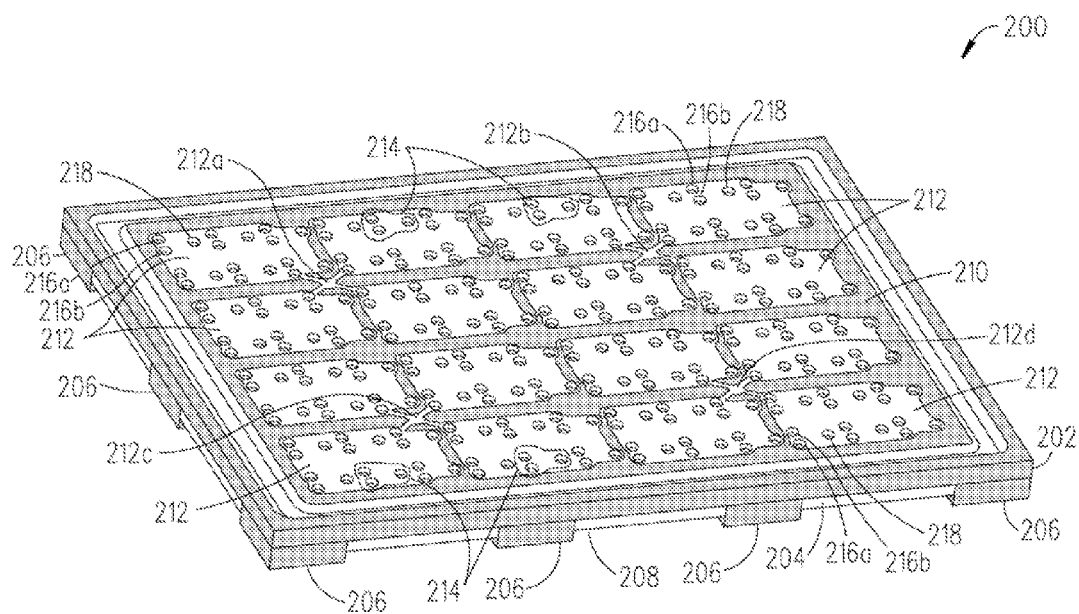
FIGS. 2A-2E are diagrams illustrating different views of a closed flow-through microplate, in embodiments of the disclosure.

In FIGS. 2A-2E, there are drawings illustrating different views of an exemplary 96-well closed flow-through microplate 200 in accordance with the disclosure (the closed flow-through microplate 200 can have any number of wells such as for example 24, 96, 384 or 1536 wells). In FIG. 2A, there is a perspective view of the 96-well closed flow-through microplate 200 which is configured as a microplate 2-plate stack that has an upper plate 202 (well plate 202) attached to a lower plate 204 (sensor plate 204) (the microplate 200 is shown with some "shaded areas" but can be, for example, transparent where the "shaded areas" are used here to help illustrate the different features of the microplate 200). The well plate 202 has a series of peripheral supports 206 extending downward therefrom which rest on a surface (e.g., table, support platform) and protect a bottom surface 208 of the sensor plate 204.

Figure 2B:
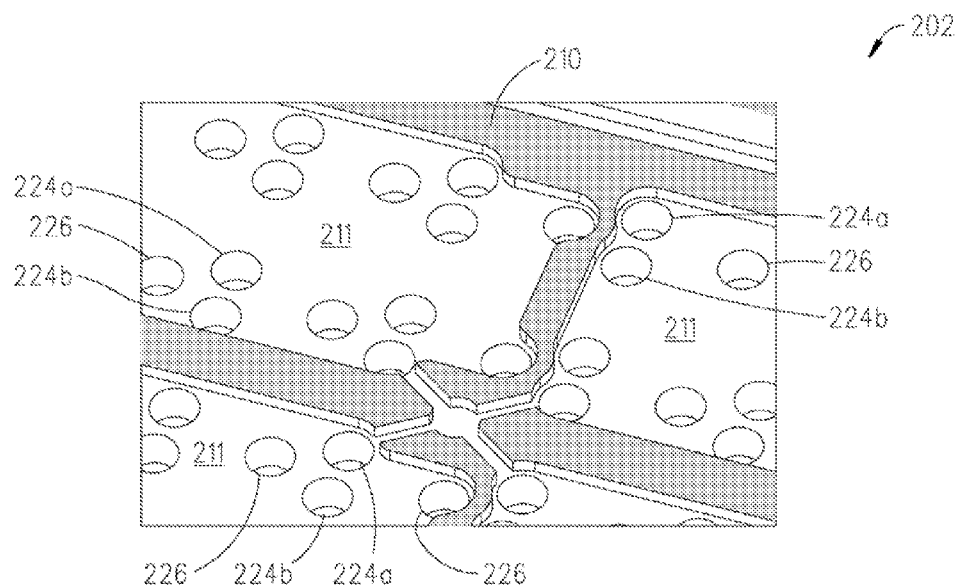

As shown in FIG. 2A, the well plate 202 has a top surface 210 on which there is a sealing substance 212 which is divided into 96-fluid delivery-removal sealing interfaces 214 (the sealing substance 212 has four distinct sections 212a, 212b, 212c and 212d). In this particular example, each of the fluid delivery-removal sealing interfaces 214 has two inlet ports 216a and 216b and one outlet port 218. However, each of the fluid delivery-removal sealing interfaces 214 could have more than two inlet ports 216 and any number of outlet ports 218. For example, each fluid delivery-removal sealing interface 214 could have three inlet ports 216 and three outlet ports 218. FIG. 2B is a partial view of the top surface 210 of the well plate 202 which shows depressions 211 located therein in which there is deposited the sealing substance 212.

Figure 2C:
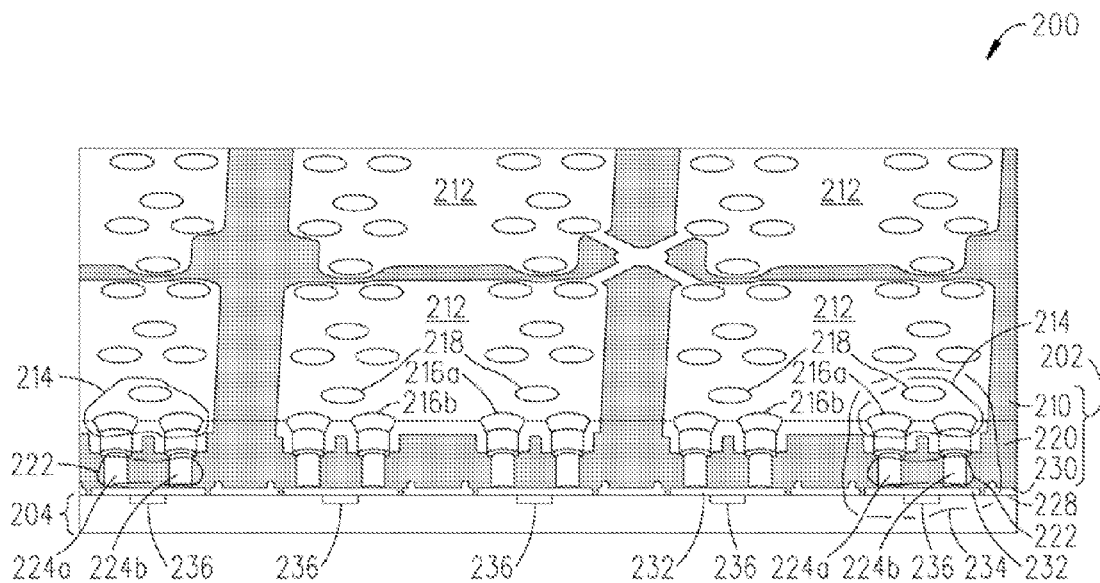
Figure 2D:
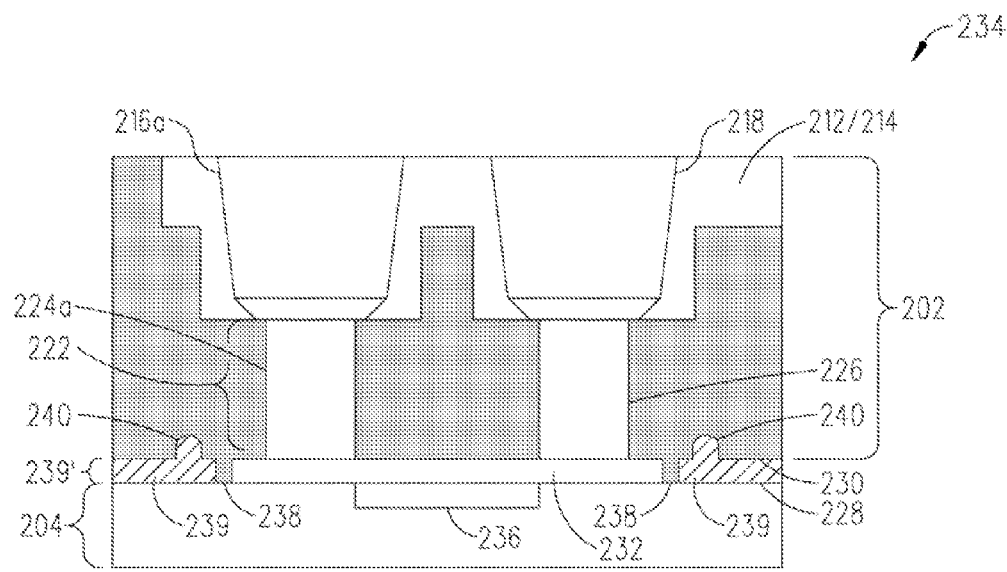
Figure 2E:
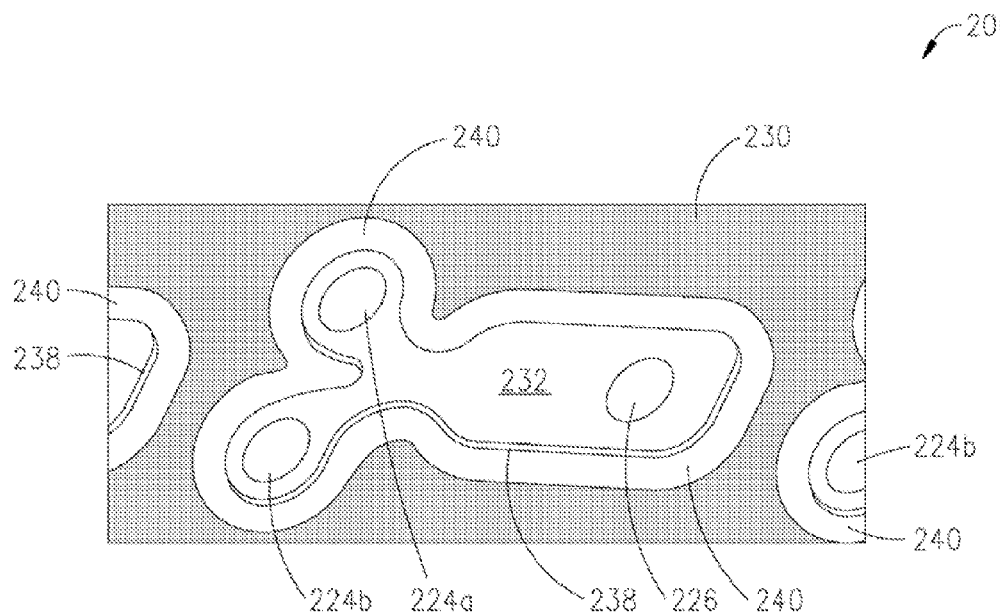

In FIG. 2C, there is shown an isometric view of a partial sectioned microplate 200. As can be seen, the well plate 202 has a body 220 with an array of 96-fluid delivery-removal channels 222. Each set of fluid delivery-removal channels 222 includes two inlet channels 224a and 224b and one outlet channel 226 (the outlet channel 226 is shown in FIG. 2D). Plus, each set of fluid delivery-removal channels 222 is aligned with a corresponding one of the fluid delivery-removal sealing interfaces 214 such that the inlet channels 224a and 224b are aligned with the inlet ports 216a and 216b and the outlet channel 226 is aligned with the outlet port 218. In addition, the microplate 200 includes the sensor plate 204 which has a top surface 228 attached to a bottom surface 230 of the well plate 202 such that there is one flow chamber 232 formed therein which corresponds with each fluid delivery-removal channel 222 that includes two inlet channels 224a and 224b and one outlet channel 226 which extend through the body 120 and open at the bottom surface 230 of the well plate 202 (the flow chamber 232 discussed below has the same or similar configuration as the flow chamber 110 discussed above with respect to FIGS. 1A-1B).

As can be seen, the sensor plate 204 also has sensors 236 incorporated therein such that there is one sensor 236 associated with each flow chamber 232 (note: if desired there can be more than one sensor 236 associated with each flow chamber 232). The sensor 236 could be a surface plasmon resonance (SPR) sensor 236 or a waveguide grating coupler (WGC) sensor 236. For a discussion of the WGC sensor 236 see U.S. Pat. No. 4,815,843. Alternatively, the use of the sensor 236 is optional as discussed below with respect to method 400.

FIG. 2D is a cross-sectional side view of one well 234 located within the microplate 200 (this is a different view than the wells 234 shown in FIG. 2C). The well 234 includes one fluid delivery-removal sealing interface 214 (sealing substance 212) that is located on the top surface 210 of the well plate 202. The fluid delivery-removal sealing interface 214 includes two inlet ports 216a and 216b (only one shown) and one outlet port 218 which are connected to one of the fluid delivery-removal channels 222 which includes two input channels 224a and 224b (only one shown) and one output channel 226 all of which open-up into the flow chamber 232. The flow chamber 232 (flow-through channel 232) because of the interconnected inlet ports 216a and 216b and inlet channels 224a and 224b and the interconnected outlet port 218 and outlet channel 226 forms a closed fluid delivery-removal system. The sensor plate 204 also has one sensor 236 incorporated therein that has a sensing surface within the flow chamber 232.

The well plate 202 and sensor plate 204 can be attached to one another by using any of several different attachment schemes. For instance, the well plate 202 may have a bottom surface 230 which has ridge(s) 238 extending therefrom which enables the formation of the flow chamber(s) 232 when the well plate 202 is attached to the sensor plate 204 (see FIGS. 2D-2E which illustrate a ridge 238 that creates a flow chamber 232 when the well plate 202 is attached to the sensor plate 204). If desired, the bottom surface 230 of the well plate 202 can also have channels 240 formed therein which extend outside a perimeter of the ridges 238 (see FIGS. 2D-2E). Each channel 240 is sized to contain the overflow of an adhesive 239 which is used to attach the well plate 202 to the sensor plate 204 (see FIG. 2D). Alternatively, a two-sided pressure sensitive adhesive film 239' can be placed between and used to attach the well plate 202 to the sensor plate 204 (see FIG. 2E). In this instance, the film 239' has sections removed therefrom in a manner that each removed section forms one of the flow chambers 232 when the well plate 202 is attached to the sensor plate 204 (the film if used would negate the need to form the ridge(s) 238 and channel(s) 240 within the bottom surface 230 of the well plate 202).

Figure 3A:
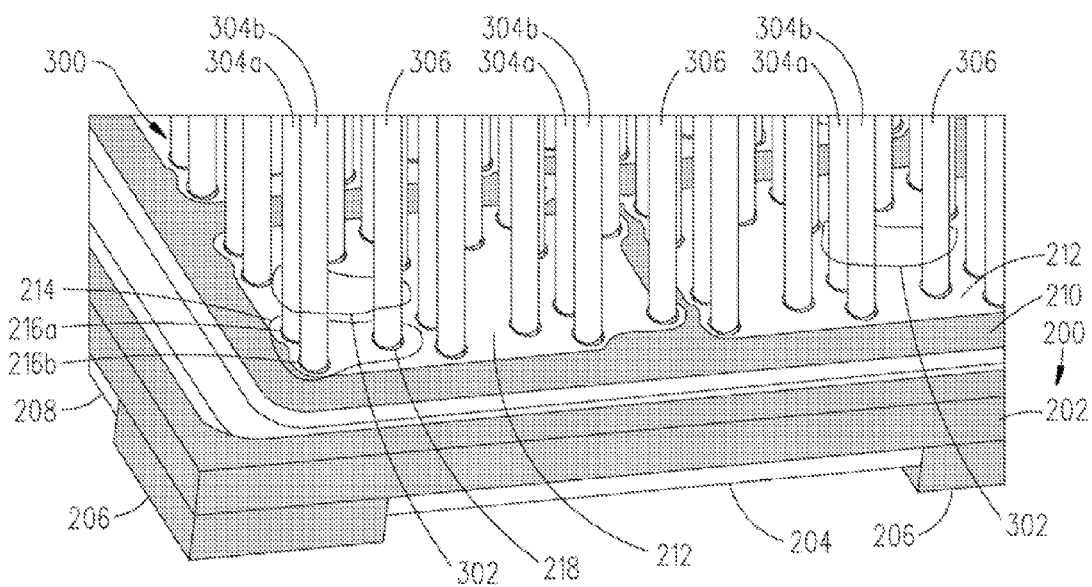
FIGS. 3A-3B are diagrams illustrating a fluid delivery system coupled to the closed flow-through microplate, in embodiments of the disclosure.
Figure 3B:
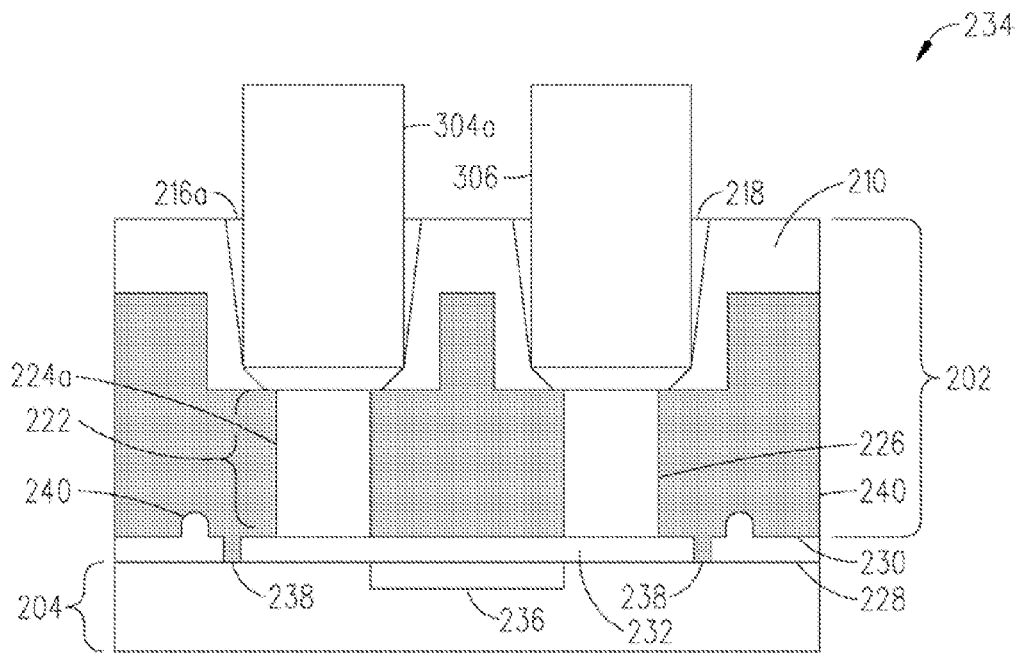

FIGS. 3A-3B illustrate a fluid delivery system 300 coupled to the closed flow-through microplate 200 in accordance with the disclosure. FIG. 3A is a partial perspective view of the fluid delivery system 300 securely connected via leak-free seals to the 96-well closed flow-through microplate 200. The fluid delivery system 300 has 96 sets of fluid delivery-removal tips 302 where each set of fluid delivery-removal tips 302 has two fluid delivery tips 304a and 304b and one fluid removal tip 306. In operation, each set of fluid delivery-removal tips 302 are inserted into the corresponding fluid delivery-removal sealing interface 214 on the microplate 200. In particular, each set of fluid delivery-removal tips 302 has two fluid delivery tips 304a and 304b and one fluid removal tip 306 respectively inserted into the two inlet ports 216a and 216b and the one outlet port 218 in the corresponding fluid delivery-removal sealing interface 214 on the microplate 200 (the sealing substance 212 selected can be o-rings and can be inserted into counter-bored channels 224a and 224b and 226 located within the well plate 202). FIG. 3B illustrates two fluid delivery tips 304a and 304b (only one shown) and the one fluid removal tip 306 have slightly smaller diameters than the inner diameter for the corresponding two inlet ports 216a and 216b and the corresponding outlet port 218 where the respective seals are effected at the bottom taper of the two fluid delivery tips 304a and 304b and the fluid removal tip 306. These sealing interfaces can be referred to as "tip seals". FIG. 3B is the same as FIG. 2D except that two fluid delivery tips 304a and 304b (only one shown) and one fluid removal tip 306 are inserted into the well 234 of the microplate 200. Alternatively, the two fluid delivery tips 304a and 304b (only one shown) and the one fluid removal tip 306 can each have a diameter that is slightly larger than the inner diameter of the two inlet ports 216a and 216b and the one outlet port 218 in the fluid delivery-removal sealing interface 214. In this case, the difference in diameters enables a liquid tight seal to be formed between the two fluid delivery tips 304a and 304b and the two inlet ports 216a and 216b and between the one fluid removal tip 306 and the one outlet port 218. These sealing interfaces can be referred to as "ring seals" as illustrated in the parent patent application. An exemplary fluid delivery system 300 that could be used in this application has been described in commonly-assigned U.S. Provisional Patent Application Ser. No. 60/817,724 filed Jun. 30, 2006, entitled "Fluid Handling System for Flow-Through Assay".

Figure 4:
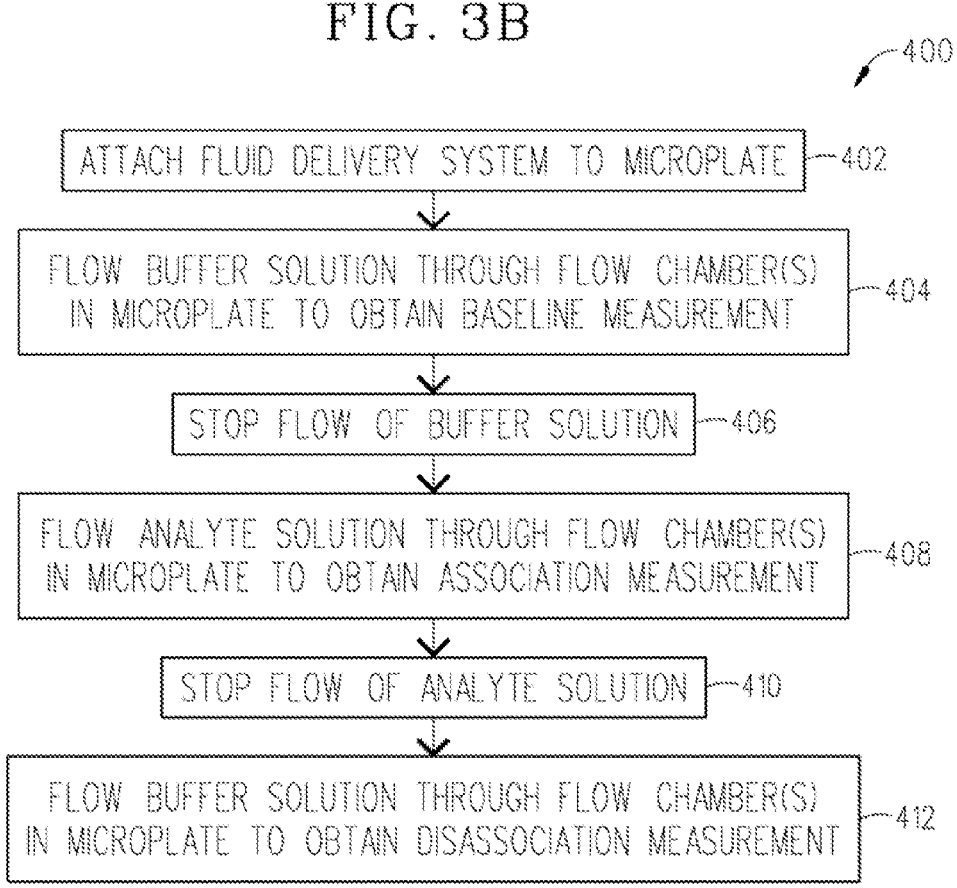
FIG. 4 is a flowchart illustrating the steps of a method for using the closed flow-through microplate to perform a flow-through kinetic assay, in embodiments of the disclosure.

FIG. 4 is a flowchart illustrating the steps of a method 400 for using the fluid delivery system 300 and the closed flow-through microplate 200 to perform a flow-through kinetic assay in embodiments of the disclosure. The method 400 can also be applied to the aforementioned dual inlet microchannel device 100. Beginning at step 402, the fluid delivery system 300 and in particular the sets of fluid delivery-removal tips 302 are attached via compression-like seals to the microplate 200 (see FIGS. 3A-3B). In this example, each set of fluid delivery-removal tips 302 has two fluid delivery tips 304a and 304b and one fluid removal tip 306 that are respectively inserted into the two inlet ports 216a and 216b and one outlet port 218 in the corresponding fluid delivery-removal sealing interface 214 on the microplate 200. Thus, the microplate 200 and in particular each flow chamber 232 is in fluid communication with two fluid delivery tips 304a and 304b and one fluid removal tip 306. For clarity, only one flow chamber 232 and how that flow chamber 232 is used to help perform a flow-through kinetic assay is discussed below but it should be appreciated that multiple flow chambers 232 would typically be used at the same time to perform multiple flow-through kinetic assays with the microplate 200.

At step 404, the fluid delivery system 300 causes a buffer solution to flow through the first fluid delivery tip 304a into and through the flow chamber 232 and then out the fluid removal tip 306 while an inspection system (not shown) interrogates the sensor 236 and obtains a baseline measurement. In one example, the inspection system can interrogate the sensor 236 to detect any changes in the refractive index at or near the sensing surface while the buffer solution is flowing within the flow chamber 232 of the microplate 200. An exemplary interrogation system which could interrogate the microplate 200 has been described in a commonly-assigned U.S. patent application Ser. No. 11/489,173. However, different types of inspection systems and different types of sensor (if used at all) could be used instead to help perform the flow-through kinetic assay. For instance, the inspection system can be a grating-based inspection system, a SPR inspection system, a fluorescent detection inspection system, an acousto-optic detection inspection system, a visual inspection system (sensors not required), or a capacitive detection inspection system.

At step 406, the fluid delivery system 300 stops the flow of the buffer solution after the inspection system obtains the baseline measurement. Then, at step 408, the fluid delivery system 300 causes an analyte solution (which would contain the drug to be tested) to flow through the second fluid delivery tip 304b into and through the flow chamber 232 and then out the fluid removal tip 306 while an inspection system (not shown) interrogates the sensor 236 and obtains an association measurement. As discussed below, the flow chamber 232 is specially configured to enable a fast switch time between the flowing of the buffer solution and the analyte solution to obtain the baseline measurement and the association measurement.

At step 410, the fluid delivery system 300 stops the flow of the analyte solution after the inspection system obtains the association measurement. Then, at step 412, the fluid delivery system 300 causes the buffer solution to flow again through the first fluid delivery tip 304a into and through the flow chamber 232 and then out the fluid removal tip 306 while an inspection system (not shown) interrogates the sensor 236 and obtains a disassociation measurement. The sensor responses and in particular the baseline measurement, association measurement, and disassociation measurement can be used to calculate the rate at which a drug (within the analyte solution) or like analyte associates with a target (immobilized on the sensing surface in the flow chamber 232) and then dissociates from the immobilized target.

This process and the resulting measurements are significant to properly test a new drug candidate. Plus, to obtain these measurements it is useful to have a fast switching time between the flowing of the buffer solution, the analyte solution, and the buffer solution during steps 404, 408 and 412. The sensor response times, particularly during the association phase, can be on the order of about 1-100 seconds. Thus, to monitor the shortest response times it is useful that the switching time from flowing the buffer solution to the analyte solution and back to buffer solution be at least as short, and preferably much shorter, than the time it takes the drug to completely bind to the immobilized target. Otherwise, the resulting kinetic response will be confounded by the slow fluidic switching. To address this issue, the flow chamber 232 has been designed to have a special configuration that minimizes the fluid switch time. Several different flow chambers 232 that can be used, each with different configurations, are discussed next with respect to FIGS. 5-11.

Figure 5A:
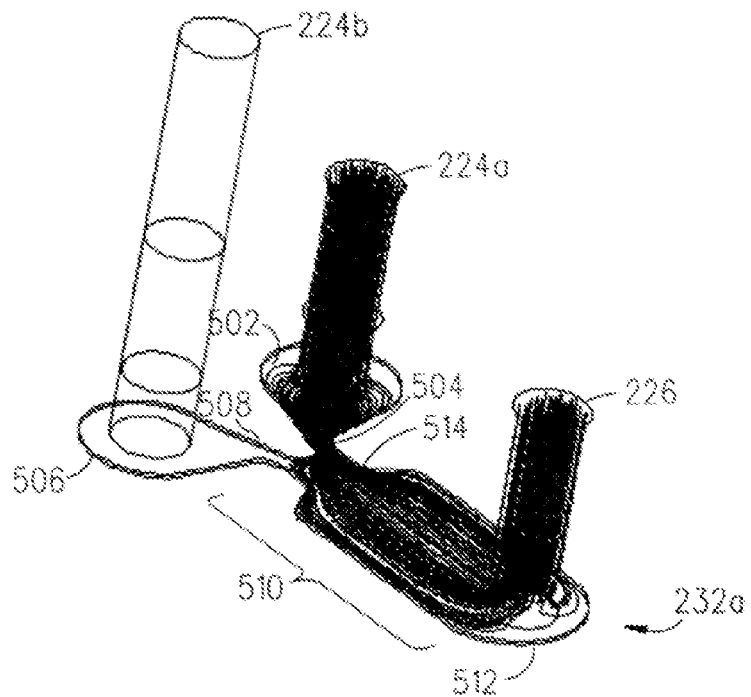
FIGS. 5A-11 are diagrams and plots which are used to help explain the configuration of a flow chamber which is used in the closed flow-through microplate (and the dual inlet microchannel device), in embodiments of the disclosure.
Figure 5B:
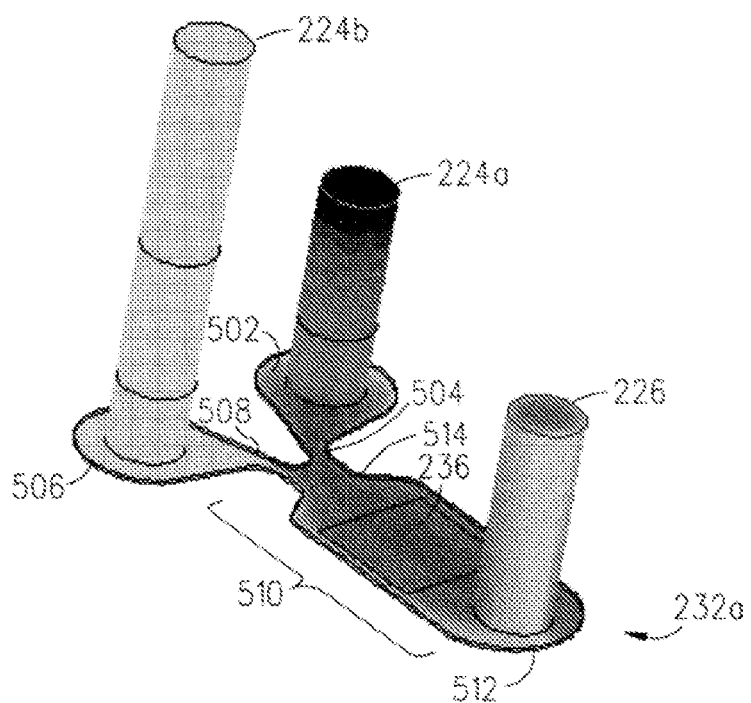
Figures 6E, 6F:
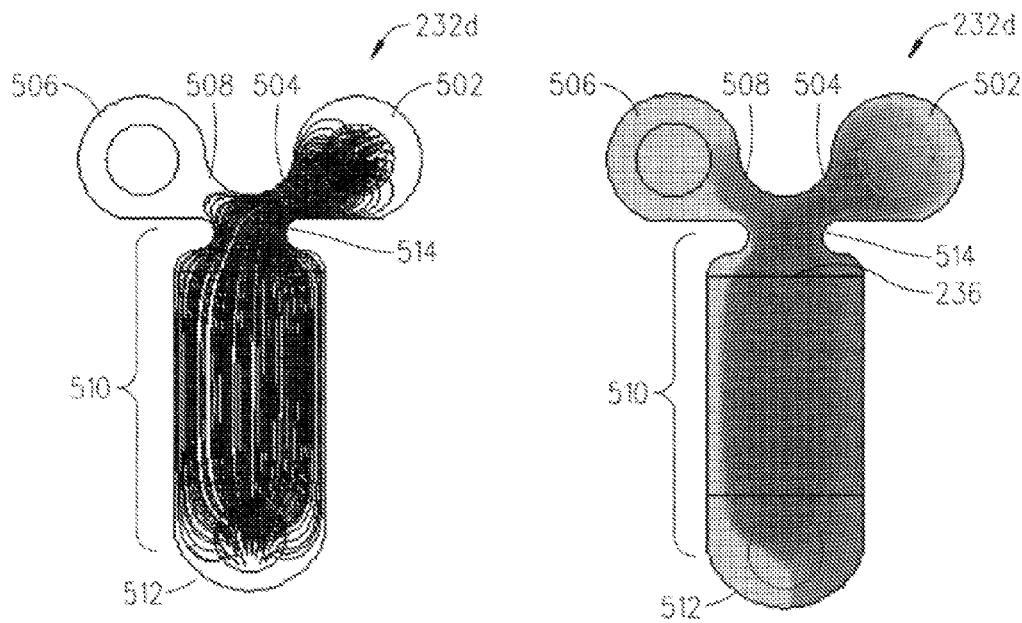
Figures 6G, 6H:
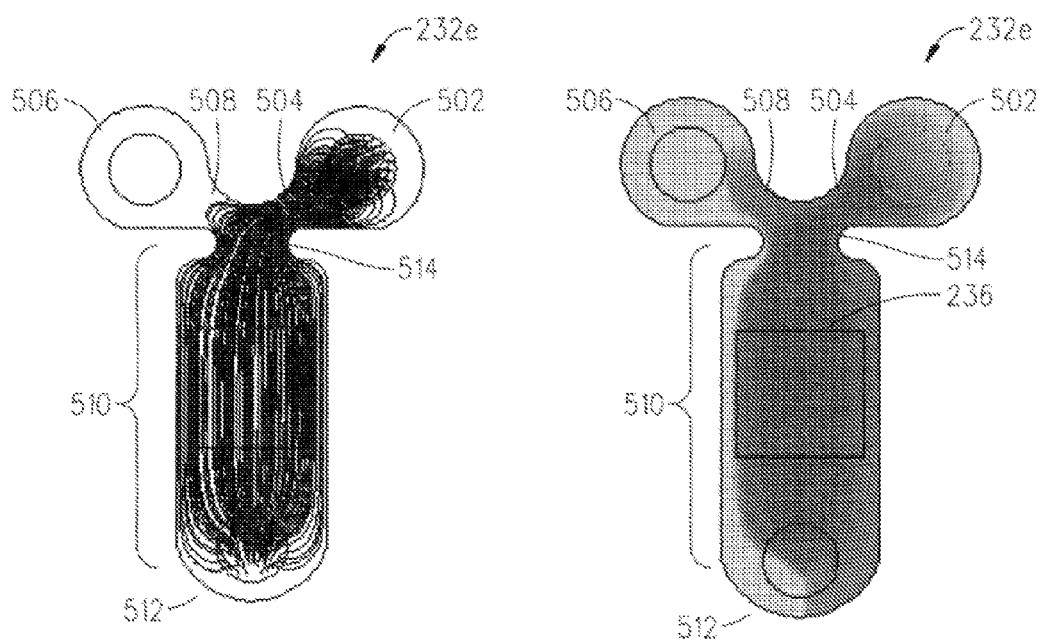

Referring to FIGS. 5A-5B, there are perspective views of an exemplary flow chamber 232a in embodiments of the disclosure. Prior to discussing the configuration of the exemplary flow chamber 232a, it should be noted that FIG. 5A illustrates the path lines of a fluid that is inserted into the first fluid inlet 224a and flowing through the flow chamber 232a before being removed via the fluid outlet 226. FIG. 5B illustrates the residence flow time associated with a fluid flowing within the flow chamber 232a where the light portions correspond with greater than about 10 seconds of residence time, the dark portions correspond with about 0 seconds of residence time, and the gray portions correspond with about 0-10 seconds of residence time.

As shown, the exemplary flow chamber 232a has a first inlet portion 502, a first flow restrictive neck 504, a second inlet portion 506, a second flow restrictive neck 508, a central portion 510, and an outlet portion 512. The first inlet channel 224a (or first fluid inlet 224a) is in fluid communication with the first inlet portion 502. The first inlet portion 502 is in fluid communication with the first flow restrictive neck 504. Likewise, the second inlet channel 224b (or second fluid inlet 224b) is in fluid communication with the second inlet portion 506. The second inlet portion 506 is in fluid communication with the second flow restrictive neck 508. The first and second flow restrictive necks 504 and 508 are in fluid communication with the central portion 510. In this example, the central portion 510 also has a flow restrictive neck 514 which is in fluid communication with the first and second flow restrictive necks 504 and 508. Also, in this example there is a sensor 236 which has a sensing surface that is located within the central portion 510. Lastly, the outlet portion 512 is in fluid communication with the central portion 510 and the fluid outlet channel 226 (or fluid outlet 226).

The flow chamber 232a can be configured to effectively minimize the switch time associated with completing steps 404, 406, 408, 410 and 412 which is significant when performing a flow-through kinetic assay. In particular, the first flow restrictive neck 504 can be sized to minimize and possibly eliminate the buffer solution from flowing into the second inlet portion 506 and up the second fluid inlet 224b during steps 404 and 412. Likewise, the second flow restrictive neck 508 can be sized to minimize and possibly eliminate the analyte solution from flowing into the first inlet portion 502 and up the first fluid inlet 224a during step 408. The flow restrictive neck 514 is sized to assure that either the buffer solution or the analyte solution flows directly over the sensing surface in the central portion 510 during steps 404, 408 and 412. For instance, the flow chamber 232a can be about 1 to about 5 mm wide, about 2 mm to about 8 mm long and about 10 to about 500 µm high. The first and second flow restrictive necks 504 and 508 can be about 100 to about 1000 µm wide and about 200 µm to about 3000 µm long. The flow restrictive neck 514 within the central portion 510 can be about 200 µm to about 1500 µm wide and about 200 µm to about 1500 µm long.

Referring to FIGS. 6A-6H, there are shown top views of four exemplary flow chambers 232b, 232c, 232d and 232e in embodiments of the disclosure. The exemplary flow chamber 232b has the same configuration as the aforementioned flow chamber 232a except that the central portion 510 does not have a flow restrictive neck 514 (see FIGS. 6A-6B). The exemplary flow chamber 232c has the same configuration as the aforementioned flow chamber 232a except that there is no sensor 236 (see FIGS. 6C-6D). The exemplary flow chamber 232d has the same configuration as the aforementioned flow chamber 232a except that the central portion 510 is narrower than the central portion 510 in flow chamber 232a (see FIGS. 6E-6F). The exemplary flow chamber 232e has the same configuration as the aforementioned flow chamber 232a except that the central portion 510 is narrower than the central portion 510 in flow chamber 232a and the sensing surface associated with the sensor 236 is smaller which can yield slightly faster switch times due to the averaging of a smaller area (see FIGS. 6G-6H). FIGS. 6A, 6C, 6E and 6G illustrate the path lines of a fluid that is inserted into the first fluid inlet 224a (associated with the first inlet portion 508) and flowing through the flow chamber 232b, 232c, 232d and 232e before being removed via the fluid outlet 226 (associated with the outlet portion 510). FIGS. 6B, 6D, 6F and 6H illustrate the residence flow time associated with a fluid flowing within the flow chambers 232b, 232c, 232d and 232e where the light portions correspond with greater than about 10 seconds of residence time, the dark portions correspond with about 0 seconds of residence time, and the gray portions correspond with about 0 to about 10 seconds of residence time.

Figure 7A:
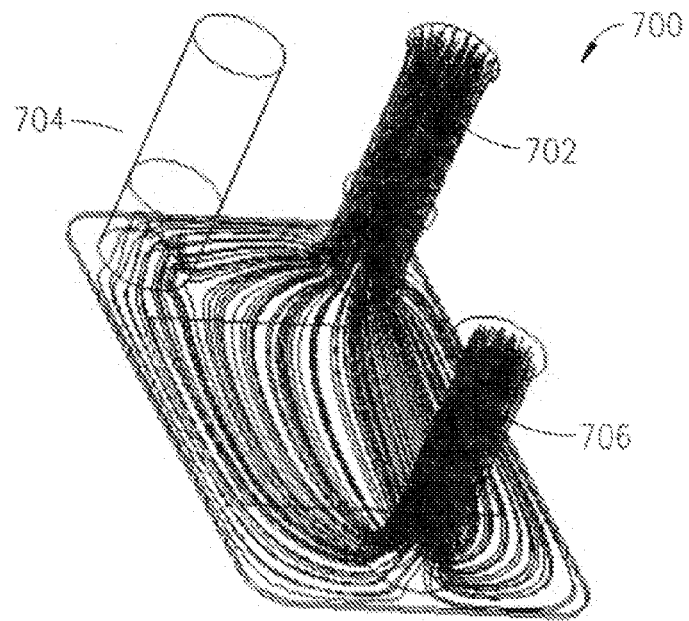
Figure 7B:
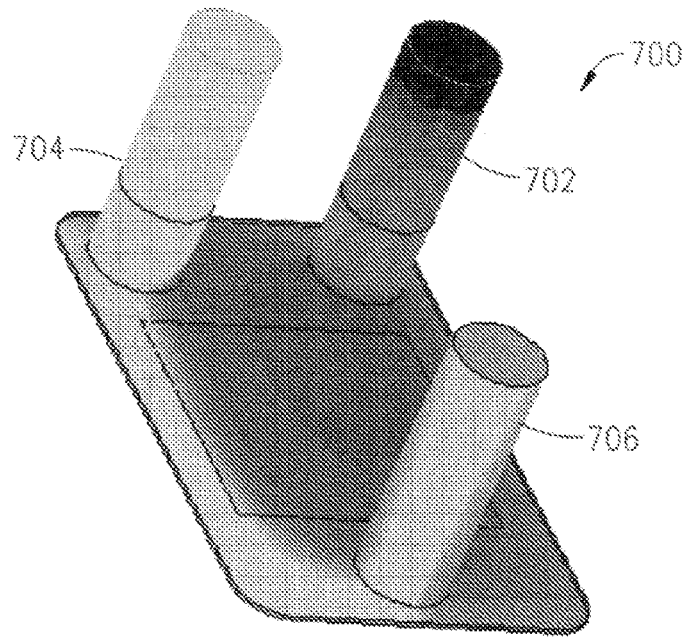

The flow chamber 232 of the disclosure is a marked-improvement over the rectangular flow chamber disclosed in the parent patent application (U.S. patent application Ser. No. 11/784,130) at least when it is used to perform a flow-through kinetic assay as described herein with respect to FIG. 4. FIGS. 7A-7B are diagrams of the rectangular flow chamber 700 which has two fluid inlets 702 and 704 and one fluid outlet 706. FIG. 7A illustrates the path lines of a fluid that is inserted into the first fluid inlet 702 and flowing through the rectangular flow chamber 700 before being removed via the fluid outlet 706. FIG. 7B illustrates the residence flow time associated with a fluid flowing within the rectangular flow chamber 700 where the light portions correspond with about 10 seconds of residence time, the dark portions correspond with about 0 seconds of residence time, and the grey portions correspond with about 0 to about 10 seconds of residence time. As can be seen, the fluid which is flowing from the first inlet 702 is also flowing near and into the second inlet 704 which may be undesirable and can adversely affect the switch times between steps 404, 406, 408, 410 and 412.

Figure 8A:
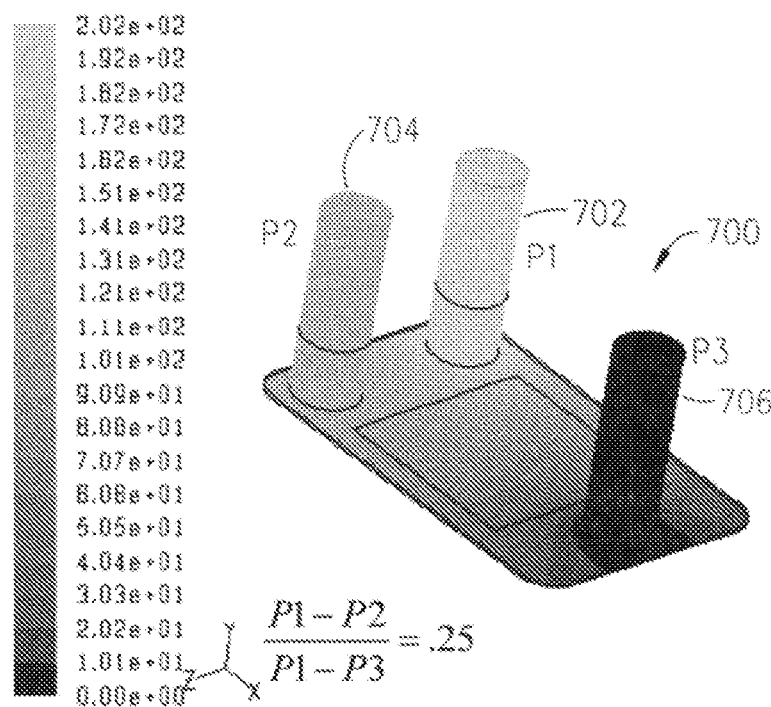
Figure 8B:
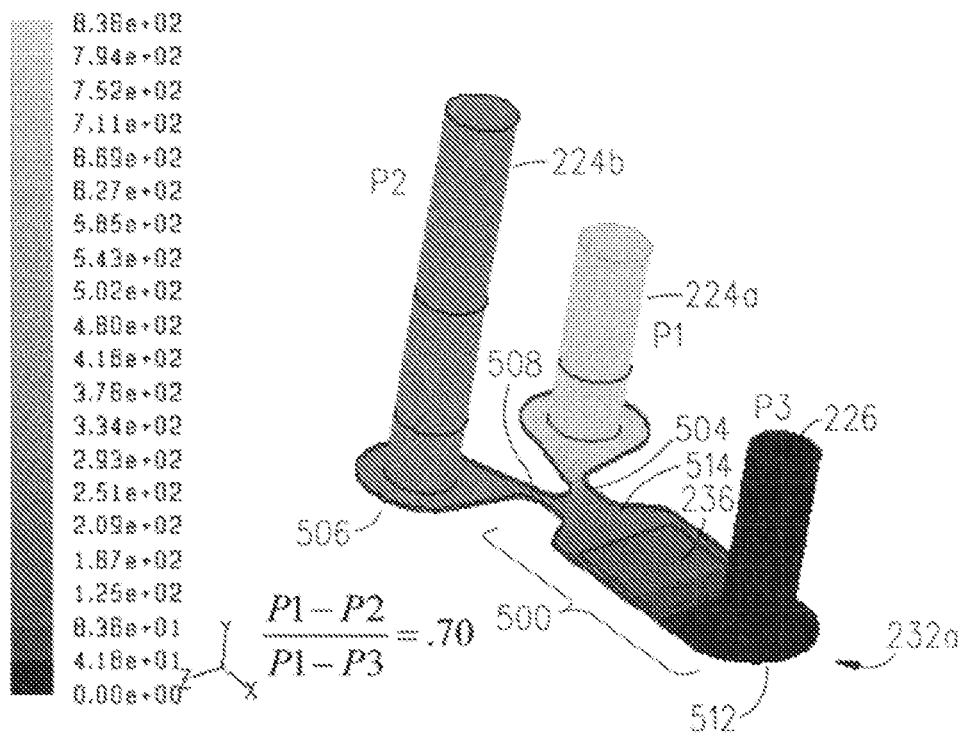
Figure 9:
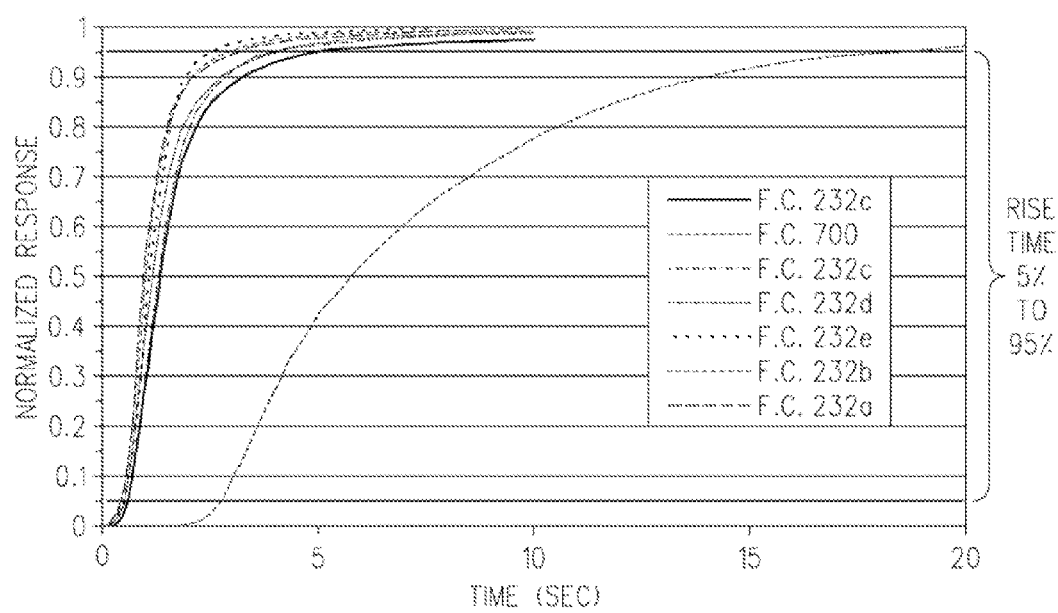

FIGS. 8A-8B respectively illustrate perspective views of the rectangular flow chamber 700 and the exemplary flow chamber 232a of the disclosure. These views illustrate the pressures measured when there is a fluid inserted into one fluid inlet 702 and 224a and flowing through the rectangular flow chamber 700 and the exemplary flow chamber 232a and out the fluid outlet 706 and 226. The exemplary flow chamber 232a has a relatively large pressure drop in the first flow restrictive neck 504 such that once the fluid leaves the first flow restrictive neck 504 the path of least resistance is to the fluid outlet 226, rather than partly to the fluid outlet 226 and the partly across the central portion 510 to the second fluid inlet 224b as is the instance with the rectangular flow chamber 700. The effect of this is a minimization of cross flow and diffusion up the second fluid inlet 224b in the exemplary flow chamber 232a which is important when trying to minimize rise time once a fluid starts to flow into the fluid inlet 224b. FIG. 9 is a plot of rise times which shows that all of the exemplary flow chambers 232a, 232b, 232c, 232d and 232e show a step-change reduction in rise time over the rectangular flow chamber 700 when flowing a fluid through one fluid inlet 224a and 702 and then stopping that flow and starting to flow another fluid through the other fluid inlet 224b and 704. This test used flow chambers with a 50 μm channel height and a 50 μL/min flow rate.

Figure 10A:
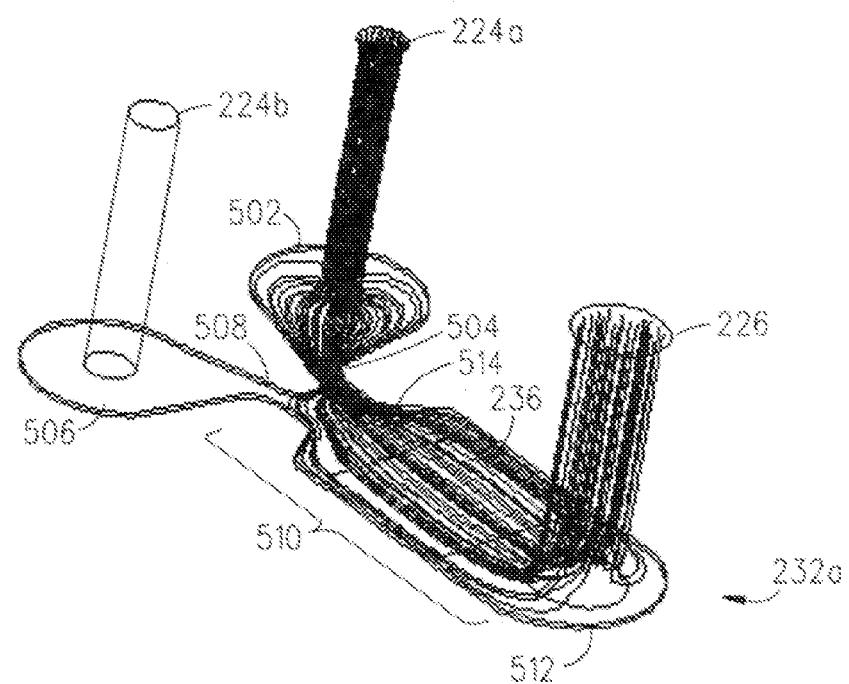
Figure 10B:
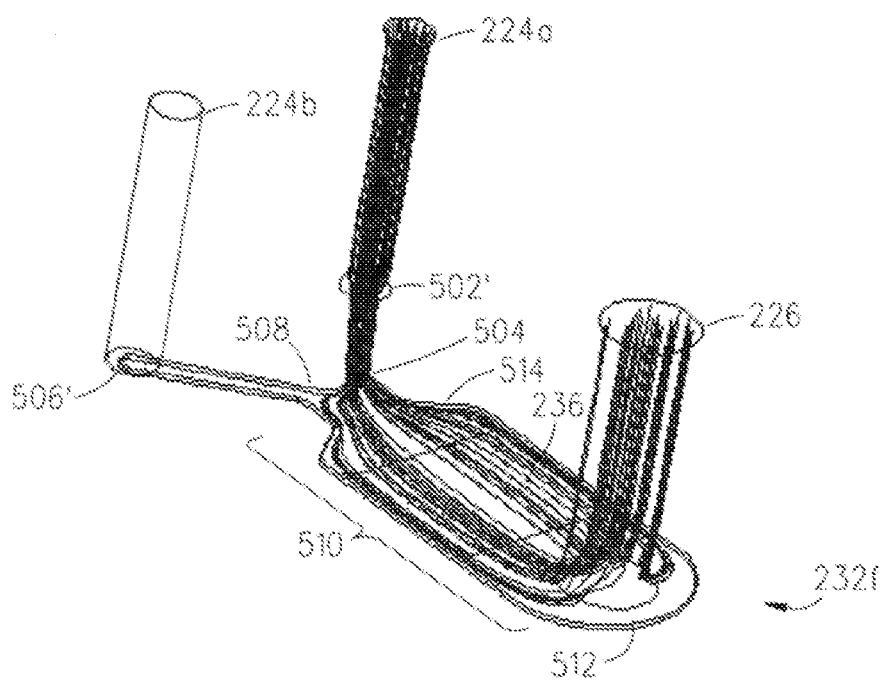

The flow chamber 232 can be further improved by reducing the sizes of the first and second inlet portions 502 and 506 which enhance the advantages of having the first and second flow restrictive necks 504 and 508. In particular, the flow chamber 232 can be further improved by reducing the diameters of the first and second inlet portions 502 and 506 which further minimizes the fluidic switch time beyond the levels demonstrated in FIG. 9. FIGS. 10A and 10B respectively illustrate perspective views of the aforementioned exemplary flow chamber 232a and an enhanced flow chamber 232f. The exemplary flow chamber 232a shown has first and second inlet portions 502 and 506 which are 1.0 mm in diameter. While, the enhanced flow chamber 232f has first and second inlet portions 502' and 506' which are 0.5 mm in diameter. This test used flow chambers with a 50 μm channel height and a 100 μl/min flow rate.

Figure 11:
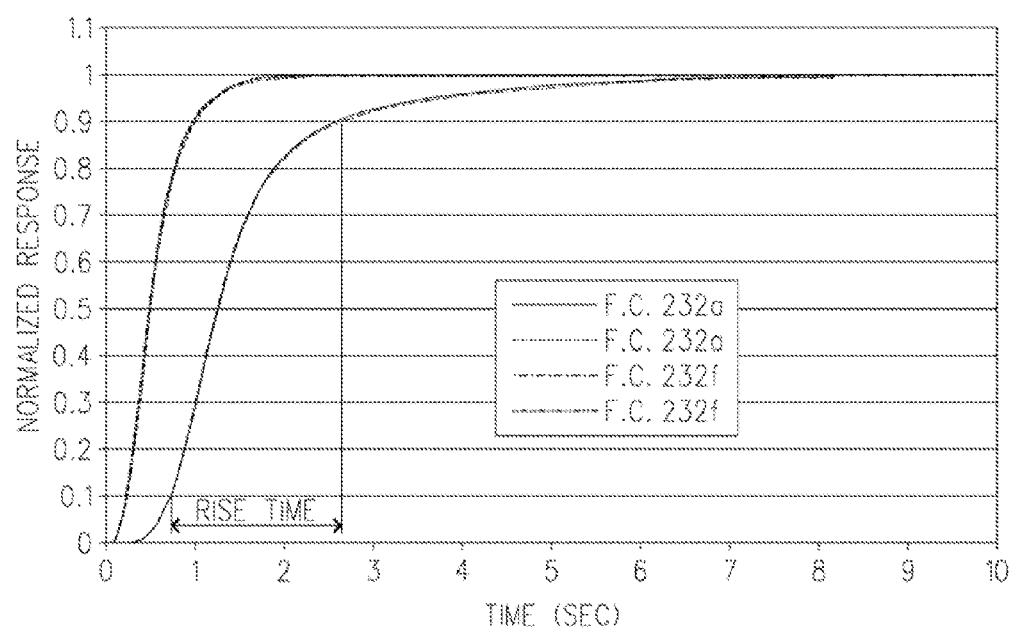

FIG. 11 is a plot that shows a comparison of the rise times for both flow chambers 232a and 232f. The fundamental reason for the reduction in rise time in flow chamber 232f is the diameter reduction in the first and second inlet portions 502' and 506'. In this test, the flow chamber 232a had first and second flow restrictive necks 504 and 508 which had a volume of 0.8 microliters and the first and second inlet portions 502 and 506 each had a volume of 2.4 microliters. Clearly, further reduction of the height or width of the first and second flow restrictive necks 504 and 508 would not significantly reduce the total volume as much as reducing the diameter of the first and second inlet portions 502 and 506. Thus, by reducing the diameters of the first and second inlet portions 502 and 506 from 1 mm to 0.5 mm the volume was reduced from 2.4 microliters to 0.6 microliters. The diameters of the first and second inlet portions 502 and 506 could further be reduced to, for example, 0.25 mm if desired. In this way, the flow chamber 232f has a total volume in the first inlet portion 502' and the first flow restrictive neck 504' of 1.4 microliters (0.8 microliters+0.6 microliters). While, the flow chamber 232a has a total volume in the first inlet portion 502 and the first flow restrictive neck 504 of 3.2 ul (0.8 microliters channel+2.4 microliters hole) which is 56% more than the corresponding sections in flow chamber 232f.

The dual inlet microchannel device 100 (with the specially configured flow chamber 110) and the microplate 200 (with the specially configured flow chambers 232) can be effectively used in flow-through kinetic assays. In addition, the dual inlet microchannel device 100 and the microplate 200 have other uses and advantages, for example:

The flow chamber 110 and 232 employs geometric flow restrictions that function like valves, reducing mechanical complexity and cost.

The design of the fluidic handling system 300 can be greatly simplified since the fluidic restrictions are integrated into the flow chamber 110 and 232.

The flow chamber 110 and 232 which has the flow centering assures efficient purging of fluid over the sensor 112 and 236 for fast rise times.

The flow chamber 110 and 232 can be incorporated within various types of devices and microplates other than the ones described herein.

The dual inlet microchannel device 100 and the microplate 200 can be used to perform other types of assays in addition to the flow-through kinetic assay described herein. For instance, dual inlet microchannel device 100 and the microplate 200 can be used in assays that require two or more fluids to flow at the same time through the flow chambers 110 and 232.

The flow chamber 110 and 232 effectively enables the fast switch times in the fluid flows by using pressure balancing which is made possible by the first inlet portion 114 and 502, the first flow restrictive neck 116 and 504, the second inlet portion 118 and 506 and the second flow restrictive neck 120 and 508. However, the pressure balancing within the flow chamber can also be accomplished in other ways such as: 1) locally decreasing the channel height by building a step or small weir around the areas that are associated with the fluid inlets 224a and 224b; or 2) embedding a porous membrane in the inlet areas that are associated with the first and second flow restrictive necks 504 and 508. Exemplary dual inlet microchannel devices that incorporate these alternative flow chambers are discussed with respect to FIGS. 12 and 13.

Figure 12A:
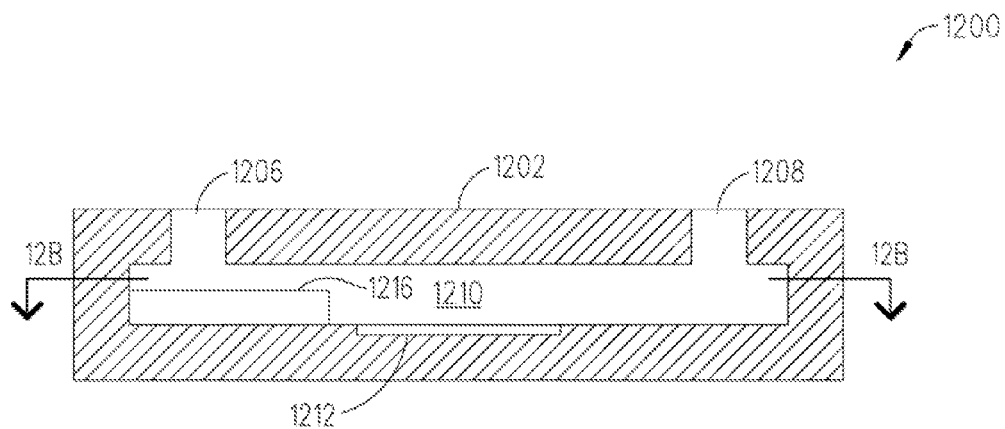
FIGS. 12A-12B are diagrams of a dual inlet microchannel device, in embodiments of the disclosure.
Figure 12B:
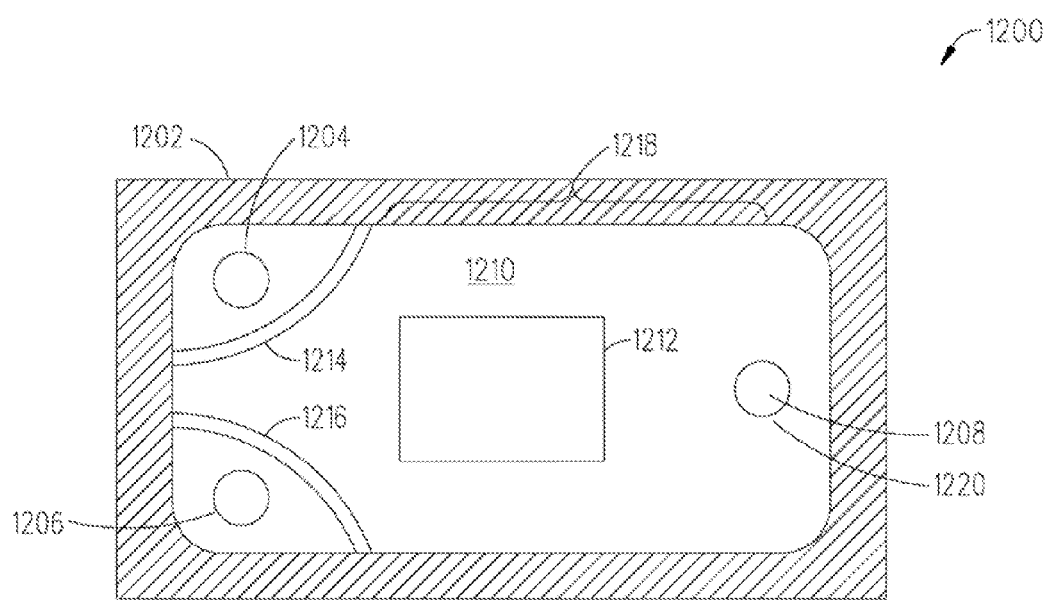

FIGS. 12A-12B respectively illustrate a cross-sectional side view and a cross-sectional top view of a dual inlet microchannel device 1200 in embodiments of the disclosure. The dual inlet microchannel device 1200 includes a body 1202 having located therein a first fluid inlet 1204, a second fluid inlet 1206, a fluid outlet 1208, a flow chamber 1210, and an optional sensor 1212. The flow chamber 1210 includes a first weir 1214 (first flow restrictor 1214), a second weir 1216 (second flow restrictor 1216), a central portion 1218, and an outlet portion 1220. The first weir 1214 and the second weir 1216 each have a height that is about 50 to about 90% of the height of the flow chamber 1210. The first weir 1214 is associated with the first fluid inlet 1204. The second weir 1216 is associated with the second fluid inlet 1206. The first weir 1214 and the second weir 1216 are both associated with one end of the central portion 1218 while an opposite end of the central portion 1218 is associated with the outlet portion 1220 and the fluid outlet 1208. The sensor 1212 if used would have sensing surface that would be located within the central portion 1218. In this example, the flow chamber 1210 has a rectangular shape but if desired the flow chamber 1210 could have the same shape as any of the aforementioned flow chambers 232 where the weirs 1214 and 1216 could be respectively placed at the interface between the fluid inlet portions 114 and 116 and the flow restrictive necks 116 and 120. The microplate 200 could incorporate these flow chambers 1210 instead of the aforementioned flow chambers 232. Plus, the method 400 could be implemented with these flow chambers 1210 instead of the aforementioned flow chambers 232.

Figure 13A:
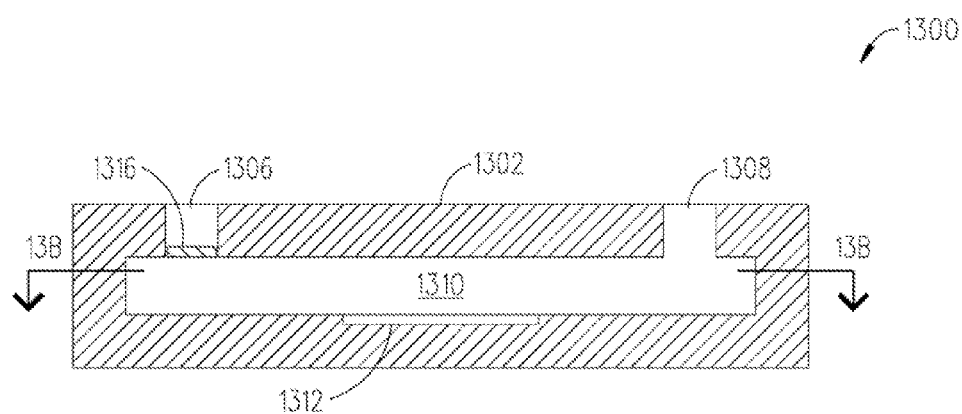
FIGS. 13A-13B are diagrams of a dual inlet microchannel device, in embodiments of the disclosure.
Figure 13B:
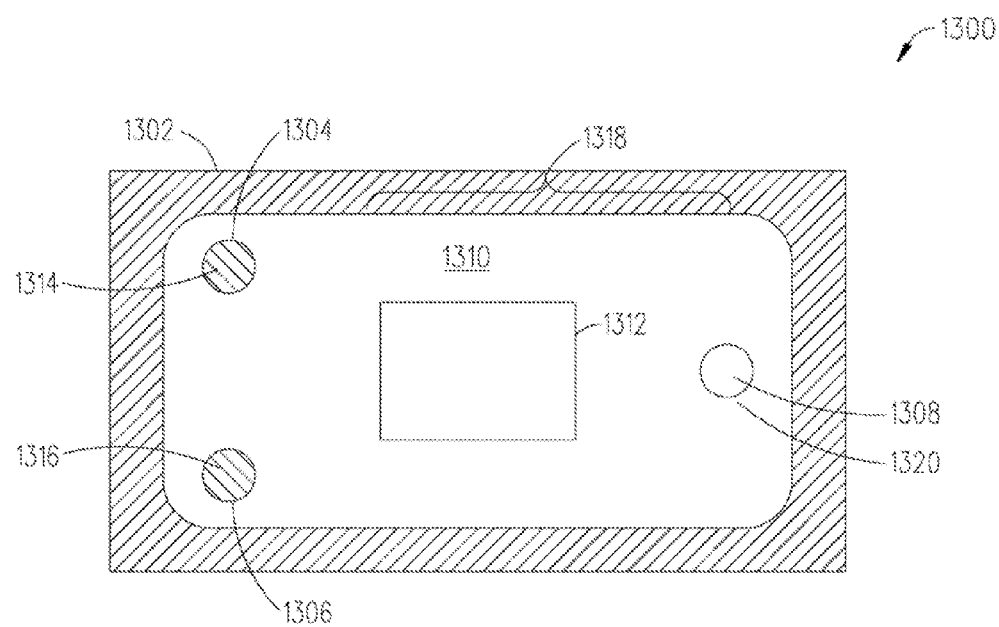

FIGS. 13A-13B respectively illustrates a cross-sectional side view and a cross-sectional top view of a dual inlet microchannel device 1300 in embodiments of the disclosure. The dual inlet microchannel device 1300 includes a body 1302 having located therein a first fluid inlet 1304, a second fluid inlet 1306, a fluid outlet 1308, a flow chamber 1310, and an optional sensor 1312. The flow chamber 1310 includes a first porous material 1314 (first flow restrictor 1314), a second porous material 1316 (second flow restrictor 1316), a central portion 1318, and an outlet portion 1320. The first porous material 1314 is associated with the first fluid inlet 1304. The second porous material 1316 is associated with the second fluid inlet 1306. The first porous material 1314 and the second porous material 1316 are both associated with one end of the central portion 1318 while an opposite end of the central portion 1318 is associated with the outlet portion 1320 and the fluid outlet 1308. The sensor 1312 if used has a sensing surface located within the central portion 1318. As shown, the first and second porous materials 1314 and 1316 have the form of plugs that are respectively located within the fluid inlets 1304 and 1306. Alternatively, the first and second porous materials 1314 and 1316 can have the form of plates that have the same diameter as the fluid inlets 1304 and 1306 and are located next to or just below the openings in the fluid inlets 1304 and 1306. In embodiments, the first and second porous materials 1314 and 1316 can have the form of sheets that are positioned to cover the openings of the fluid inlets 1304 and 1306 and can be sized to be larger than the openings of the fluid inlets 1304 and 1306 but not so large as to be located over the sensor 1312. In this example, the flow chamber 1310 has a rectangular shape but if desired the flow chamber 1310 could have the same shape as any of the aforementioned flow chambers 232. The microplate 200 could incorporate these flow chambers 1310 instead of the aforementioned flow chambers 232. Plus, the method 400 can be implemented with these flow chambers 1310 instead of the aforementioned flow chambers 232.

Although several embodiments of the disclosure have been illustrated in the accompanying Figures and described in the Detailed Description, it should be understood that the invention is not limited to the embodiments disclosed, but is capable of numerous rearrangements, modifications and substitutions without departing from the spirit of the invention as set forth and defined by the following claims.

The invention claimed is:

1. A method for performing a kinetic assay, the method comprising the steps of:
   attaching a fluid handling system to a device, where the fluid handling system includes a first fluid delivery tip, a second fluid delivery tip, and a fluid removal tip all of which are connected to the device, wherein the device has a body including:
   a first fluid inlet connected to the first fluid delivery tip;
   a second fluid inlet connected to the second fluid delivery tip; and
   a fluid outlet connected to the fluid removal tip; and
   wherein the body has a flow chamber formed therein, wherein the flow chamber including:
      a first flow restrictor associated with the first fluid inlet;
      a second flow restrictor associated with the second fluid inlet;
      a central portion having one corner of one end associated with the first flow restrictor and another corner of the one end associated with the second flow restrictor;
      the central portion having a sensing surface on which there is immobilized a target; and
      an outlet portion associated with the fluid outlet and an opposite end of the central portion, wherein the opposite end is directly opposite from both an opening of the one corner and an opening of the another corner associated with the one end of the central portion;
   flowing a buffer solution through the first fluid delivery tip and into and through the flow chamber and then out the fluid removal tip while an inspection system obtains a baseline measurement;
   stopping the flow of the buffer solution;
   flowing an analyte solution through the second fluid delivery tip and into and through the flow chamber and then out the fluid removal tip while the inspection system obtains an association measurement;
   stopping the flow of the analyte solution; and
   flowing the buffer solution through the first fluid delivery tip and into and through the flow chamber and then out the fluid removal tip while the inspection system obtains a disassociation measurement.

2. The method of claim 1, wherein the first flow restrictor is a first porous material and the second flow restrictor is a second porous material.

3. The method of claim 1, wherein the first flow restrictor is a first weir and the second flow restrictor is a second weir.

4. The method of claim 1, wherein the flow chamber further includes:
   a first inlet portion located between the first fluid inlet and the first flow restrictor; and
   a second inlet portion located between the second fluid inlet and the second flow restrictor.

5. The method of claim 4, wherein the first flow restrictor is a first flow restrictive neck and the second flow restrictor is a second flow restrictive neck.

6. The method of claim 5, wherein the first flow restrictive neck is sized to at least minimize the buffer solution from flowing into the second inlet portion and up the second fluid inlet.

7. The method of claim 5, wherein the second flow restrictive neck is sized to at least minimize the analyte solution from flowing into the first inlet portion and up the first fluid inlet.

8. The method of claim 5, wherein the central portion further includes a third flow restrictive neck which is in fluid communication with the first flow restrictive neck and the second flow restrictive neck.

9. The method of claim 8, wherein the third flow restrictive neck is sized to assure the buffer solution or analyte solution flows directly over the sensing surface.

10. The method of claim 1, wherein the inspection system comprises at least one of:
    a grating-based inspection system;
    a surface plasmon resonance inspection system;
    a fluorescence inspection system;
    an acousto-optic inspection system;
    a capacitive inspection system;
    a visual inspection system; or
    a combination thereof.

* * * * *